(12) United States Patent
Takahashi (10) Patent No.: US 6,503,082 B1
(45) Date of Patent: Jan. 7, 2003

(54) PORTABLE TOOTH/NAIL SURFACE CLEANING POLISHER

(76) Inventor: Atsushi Takahashi, 20-15-1, Kizaki, Tsuruga-shi, Fukui (JP)

( * ) Notice: Subject to any disclaimer, the term of this patent is extended or adjusted under 35 U.S.C. 154(b) by 0 days.

(21) Appl. No.: 09/669,853

(22) Filed: Sep. 27, 2000

(51) Int. Cl.[7] .................................................. A61C 3/06
(52) U.S. Cl. ........................ 433/125; 433/126; 206/368; 132/73.6
(58) Field of Search ................................. 433/125, 126, 433/127, 130, 131, 132; 206/368, 369, 370, 635; 132/328, 311, 73.6, 75

(56) References Cited

U.S. PATENT DOCUMENTS

| 3,472,045 | A | * | 10/1969 | Nelsen et al. | |
|---|---|---|---|---|---|
| 3,599,333 | A | * | 8/1971 | Muhler | |
| 3,613,696 | A | | 10/1971 | Paule et al. | |
| 3,939,599 | A | * | 2/1976 | Henry et al. | 433/99 |
| 3,977,084 | A | * | 8/1976 | Sloan | 433/131 |
| 4,033,007 | A | * | 7/1977 | Hadary | 15/172 |
| 4,281,989 | A | * | 8/1981 | Glover et al. | 433/130 |
| 4,303,393 | A | * | 12/1981 | Gentry | 433/130 |
| 5,775,905 | A | * | 7/1998 | Weissenfluh et al. | 433/166 |
| 5,797,744 | A | | 8/1998 | Rosenberg | |
| 5,902,107 | A | * | 5/1999 | Lowell | 433/130 |
| 6,146,140 | A | * | 11/2000 | Bailey | 433/166 |

FOREIGN PATENT DOCUMENTS

| DE | 2 005 266 | 9/1970 |
|---|---|---|
| DE | 2 209 562 | 9/1973 |
| WO | WO 97/09002 | 3/1997 |

* cited by examiner

*Primary Examiner*—John J. Wilson
*Assistant Examiner*—Melba Bumgarner
(74) *Attorney, Agent, or Firm*—Snider & Associates; Ronald R. Snider (57) ABSTRACT

A portable tooth or nail polisher has a motor connected to a coupler formed in a body. A head member is mounted on the coupler during use. An accommodating space is formed in the body for holding the head when not in use. A head holder for fixing the head member in the accommodating space presses in a direction perpendicular to a longitudinal direction and is constructed of a pair of protrusions extending from the body defining the accommodating space. The distance between the protrusions is smaller than the width of the head member.

2 Claims, 9 Drawing Sheets

PORTABLE TOOTH/NAIL SURFACE CLEANING POLISHER

BACKGROUND OF THE INVENTION

1. Field of the Invention

The present invention relates to an instrument for removal of a coloring matter deposit such as a nicotine-stain attached on a tooth surface caused by intake of cigarette smoke, which generally cannot be removed by a combination of a tooth brush and tooth paste; and for polishing a nail surface to attain gloss.

2. Prior Art

In the prior art, removal of a coloring matter deposit such as a nicotine-stain attached on a tooth surface caused by intake of cigarette smoke, which generally cannot be removed by a combination of a tooth brush was performed by a professional in a dentist clinic. Further, a polishing operation of a nail surface was performed using a file or the like.

When a tooth surface and a nail surface was cleaned and polished, a polishing agent was required to be daubed on a tooth/nail surface cleaning/polishing tip, or alternatively direct on the tooth surface or the nail surface each time when a polishing operation on the tooth surface or the nail surface was performed.

A tooth surface cleaner employed by a dentist and a dental technician in a dentist clinic was of a type that an angle of a tooth surface cleaning/polishing tip shaft to a holding section was fixed, and when the tooth surface cleaner was handled in the oral cavity of a patient by himself or herself, there was difficulty in cleaning/polishing not only from the anterior teeth section to the molar teeth section but also the tongue sides and palate sides of the teeth sections therebetween. Further, when the tooth surface cleaner is operated for surface cleaning/polishing of a nail of an operator, himself or herself, there was again difficulty in cleaning/polishing the nail surface with such an instrument with a single kind of cleaning/polishing tip shaft having a fixed angle according to which of hands was more skillful than the other, or a growing direction of a nail.

A tooth surface polisher used in a dentist clinic or the like was with a cord for power supply and there was not available a compact, cordless, tooth surface cleaning polisher for which portability was considered.

It is accordingly an object of the present invention to provide an instrument enabling removal of a coloring matter deposit such as a nicotine-stain attached on a tooth surface caused by intake of cigarette smoke, which generally cannot be removed by a combination of a tooth brush and tooth paste with such ease as to use a tooth brush and enabling easy cleaning/polishing operation in the vicinity of a margin of a nail where a cleaning/polishing operation using a file or the like is difficult; and further enabling use of the instrument under any working environment adopting a cordless scheme.

It is another object of the present invention to enable a tooth/nail surface polishing operation without daubing a polishing agent used for polishing a nail surface and a tooth surface on a tooth/nail surface cleaning/polishing tip, or alternatively direct on the tooth surface or the nail surface each time when a polishing operation on the tooth surface or the nail surface is performed.

It is still another object of the present invention to enable, when a tooth surface cleaner is handled in an oral cavity, a tooth surface cleaning tip of the tooth surface cleaner to reach every corner in the oral cavity so as to polish not only from an anterior teeth section to a molar teeth section but also the tongue sides and palate sides of teeth sections therebetween with ease and enable, when the tooth surface cleaner is used for nail surface cleaning/polishing, easy cleaning/polishing of portions where the cleaning/polishing is difficult according to which of hands was more skillfull than the other, or a growing direction of a nail.

It is yet another object of the present invention to enable realization of a portable tooth/nail surface cleaning polisher as compact as or smaller in outer volume than a 20-cigarettes package so as to be handled in an automatic vending machine or the like which has been widely spread in public.

SUMMARY OF THE INVENTION

The present invention has been made to achieve the above objects and a first aspect of the present invention is directed to a portable tooth/nail surface cleaning polisher including: a body of a cordless type having a battery and a micro-motor therein; and a demountable, tooth/nail surface cleaning/polishing tip of a cup-like, a circular cone-like or a disc-like shape, made from rubber, soft resin or the like, mounted at a distal end of a rotary shaft of the micro-motor. By pressing the tooth/nail surface cleaning polisher to the tooth surface or the nail surface lightly, a coloring matter deposit such as a nicotine-stain attached on a tooth surface caused by intake of cigarette smoke can be removed and a nail surface can also be cleaned and polished.

A second aspect of the present invention is directed to a portable tooth/nail surface cleaning/polishing tip of a cup-like, a circular cone-like or a disc-like shape, made form rubber, soft resin or the like in the interior of which a polishing agent is stored, wherein the tooth/nail surface cleaning/polishing tip is compressed and deformed by pressing the tooth/nail surface cleaning/polishing tip to a tooth surface or a nail surface by a hand pressure to discharge an optimal amount of the polishing agent stored in the interior to a polishing surface at any desired time, thereby enabling cleaning/polishing of the tooth surface or the nail surface without daubing the polishing agent on the tooth/nail surface cleaning/polishing tip, or alternatively direct on the tooth surface or the nail surface each time of the cleaning/polishing.

A third or fourth aspect of the present invention is directed to a portable tooth/nail surface cleaning polisher, wherein a swing angle of a rotary shaft of the tooth/nail surface cleaning/polishing tip to a holding section and a rotary shaft of the micro-motor can be adjusted to any value approximately in the range of 0° to 130° in exterior angle using a universal joint, gears or the like, or there are provided parts for exchange with which a swing angle of the rotary shaft of the tooth/nail surface cleaning/polishing tip to the holding section and the rotary shaft of the micro-motor can be adjusted to any value approximately in the range of 0° to 130° in exterior angle. With such constructions and functions, when the tooth/nail surface cleaning/polishing tip is handled in an oral cavity, the tooth/nail surface cleaning/polishing tip can clean and polish not only from an anterior teeth section to a molar teeth section but also the tongue sides and palate sides of teeth sections therebetween reaching those with ease, while when the tooth/nail surface cleaning/polishing tip is used for nail surface cleaning/polishing, easy cleaning/polishing can be realized of portions where the operation is difficult according to which of hands was more skillfull than the other, or a growing direction of a nail:, for example a surface of a foot little finger or the like.

A fifth aspect of the present invention is directed to a portable tooth/nail surface cleaning polisher, wherein portability of the tooth/nail surface cleaning polisher is increased using the battery and the micro-motor; and a battery section, the micro-motor and the tip are divided into two or more parts. With such a construction, a total outer volume of the tooth/nail a surface cleaning polisher can be reduced to a volume equal to or less than, for example, a 20 cigarette package in a disassembled state.

Furthermore, portability can be increased by enabling a polishing head to be accommodated in the body. In such an aspect of the present invention, a battery holder holding a battery and a motor driven by the battery are incorporated in the body which not only is portable, but is gripped by a hand when being used in polishing. In addition to this, a coupler including a rotation output section rotated and driven by the motor is formed in the body. A head member including a polishing rotor rotating while keeping in contact with a to-be-polished surface is mounted on the coupler in a demountable manner. An accommodating space accommodating the head member demounted from the coupler is formed in the body and further, a cover is mounted on the body in a demountable manner so as to enclose the head member accommodated in the accommodating space from outside. With such a construction, a portable tooth/nail surface cleaning polisher is more compact as a whole in carrying by a person or in storage and when carrying the cleaning polisher in a bag together with a face-wash related tool case or the like, the cleaning polisher and others are not voluminous. Further, the polishing head is covered with a cover and not put into direct contact with other things; therefore, no deterrent is exerted against putting the cleaning polisher into a bag and at the same time, the cleaning polisher is clean.

In a case where a head holder fixing the head member in the accommodating space of the body is formed therein, the head member can be held in a stable manner with no rattling in carrying by a person since the head member is mounted to the head holder to be fixed in storage.

In a further modification of the present invention, the head member includes: a head arm mounted on the coupler in a demountable manner, a polishing rotor located at the distal end of the head arm and rotating while keeping in contact with a to-be-polished surface, and a rotation transmitting mechanism transmitting rotation to the polishing rotor from the rotation output section of the coupler. The head member demounted from the coupler is, similar to the above described, accommodated in the accommodating space and in this state (preferably, the head member is fixed by the head holder), a cover is mounted to the body in a demountable manner from outside. A coupling construction of the head arm and the coupler can be set, in this case, such that a swing angle of mounting of the head arm to the coupler can be selected at any of a prescribed plurality of angular positions or adjusted at any angular position. In other words, by selecting or adjusting an angular position in the head arm mounting, a direction in which the polishing rotor is directed relative to the body is varied. With such construction and function, polishing of a front side of teeth, a rear side of if teeth or a molar teeth section in an oral cavity, or nails of foot fingers, or other various portions can be performed with ease by setting a direction of the polishing rotor.

DETAILED DESCRIPTION OF THE PREFERRED EMBODIMENT

EXAMPLE

Figure 1:
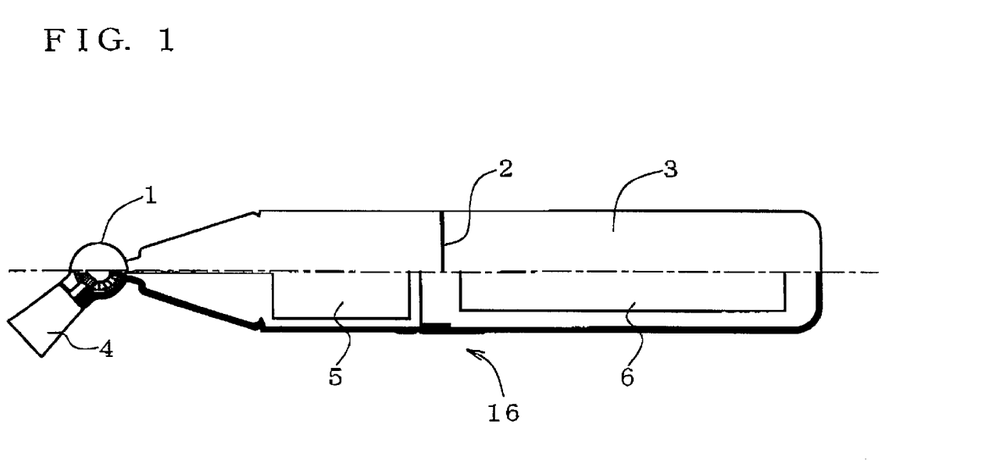
FIG. 1 is a side view of a portable tooth/nail surface cleaning polisher of the present invention.

Description will be given of an example of the present invention: A portable tooth/nail surface cleaning polisher (hereinafter simply referred to as a leaning polisher) shown in FIG. 1 includes: a body 16 having a battery 6 and a micro-motor 5 therein; and a demountable, tooth/nail surface clean/polishing tip 4 (hereinafter simply referred to as a cleaning/polishing tip) of a cup-like, a circular cone-like or a disc-like shape, made form rubber, soft resin or the like, mounted on a distal end of a rotary shaft of the micro-motor 5. By pressing the cleaning polisher to the tooth surface holding a holding section 8 of the body 16 of the cleaning polisher by a hand, a coloring matter deposit such as a nicotine-stain attached on a tooth surface caused by intake of cigarette smoke, which generally cannot be removed by a combination of a tooth brush and tooth paste, is removed in a manner of handling a tooth brush. Likewise, when a nail surface cleaning polisher is used, the cleaning/polishing tip is lightly pressed on the nail surface by hand pressure.

Figure 3:
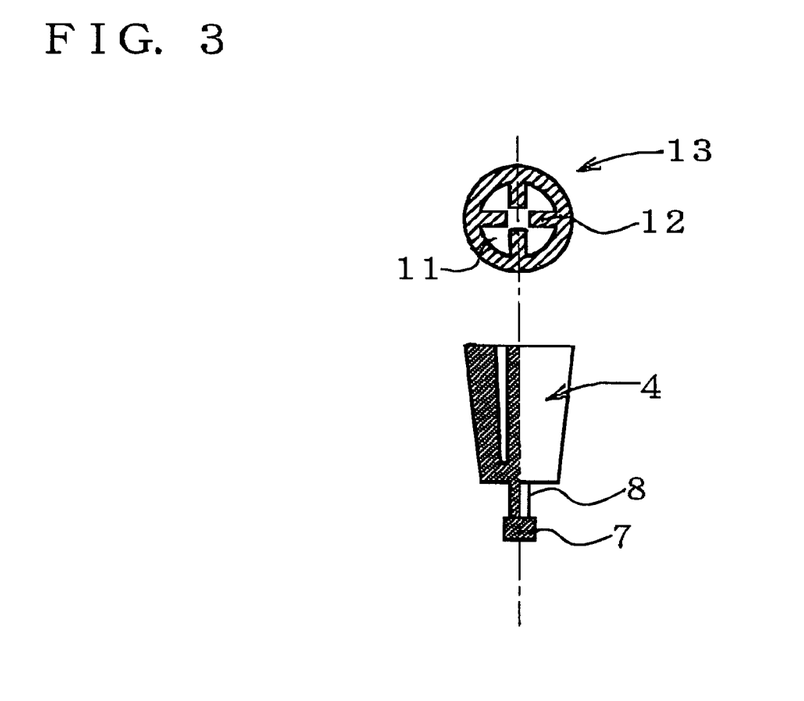
FIG. 3 is views of a part of the tooth/nail surface cleaning polisher of FIG. 1.
Figure 4:
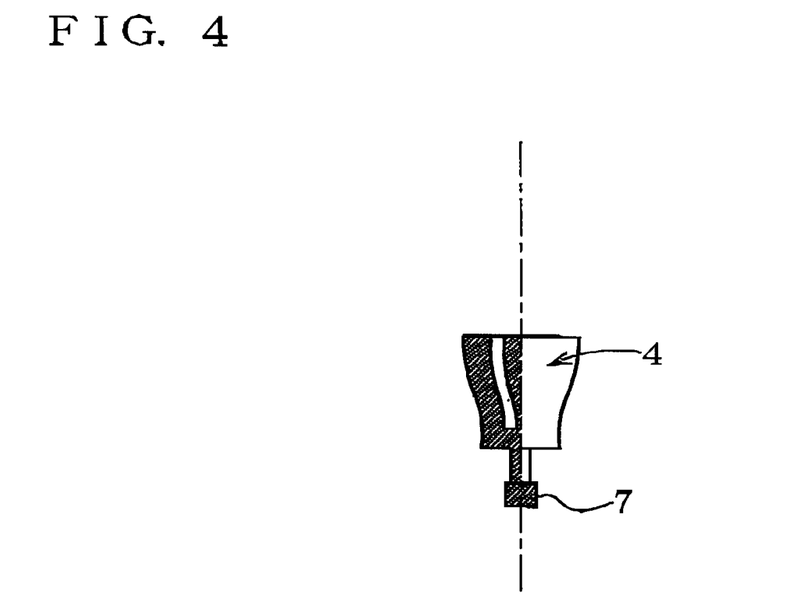
FIG. 4 is a view illustrating a state of the tooth/nail surface cleaning polisher of FIG. 1 under pressure.

According to the second aspect of the present invention, in FIG, 3, when the cleaning/polishing tip 4 of a cup-like, a circular cone-like or a disc-like shape, made form rubber, soft resin or the like in the interior of which a polishing agent is stored is pressed to a tooth surface by a hand pressure, the cleaning/polishing tip 4 is, as shown in FIG. 4, compressed and elastically deformed to discharge an optimal amount of the polishing agent stored in the interior to a polishing surface at any desired time. The clean/polishing tip 4 can be constructed such that a polishing agent holding member 13 is embedded in the interior of the cleaning/polishing tip 4, a polishing agent storage space 11 is formed in the polishing agent holding member 13 and an elastic porous soft material such as sponge, soft expanded urethane rubber surrounds the polish agent storage space 11 filled with the polishing agent in advance. The polishing agent holding member 13 is made from, for example, a relatively thin, elastically deformable, resin or rubber member, an outer shell of an annular section has a plurality of fins on the inner sauce thereof extending inward and spaces between the fins can serve as the polishing agent storage space 11. By pressing such a cleaning/polishing tip 4 onto a tooth or nail surface, the polishing agent stored in the interior flows out slowly.

Figure 2:
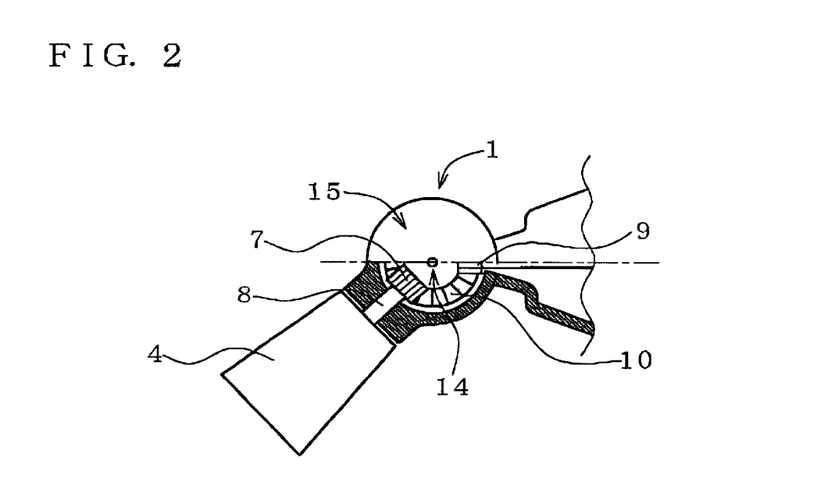
FIG. 2 is an enlarge view of a head section of the tooth/nail surface cleaning polisher of FIG. 1.

According to the third and fourth aspects of the present invention, the cleaning polisher with the cleaning/polishing tip 4 has a construction and function described below in order that when the cleaning/polishing tip 4 is handled in an oral cavity, the cleaning/polishing tip 4 can lean and polish not only from an anterior teeth section to a molar teeth section but also the tongue sides and palate sides of teeth sections therebetween reaching those with ease and that in a nail surface polishing operation, easy cleaning/polishing can be realized in the vicinity of a margin of a nail where a cleaning/polishing operation using a file or the like is difficult: A driving force of the micro-motor 5 is, as shown in FIG. 2, transmitted to a tooth/nail surface cleaning/polishing tip driving gear 7 from a micro-motor driving gear 9 through a conversion gear 10. A swing angle of a rotary shaft of the cleaning/polishing tip 4 to the body holding section 3 (FIG. 1) and the motor rotary shaft is adjusted to any value approximately in the range of 0° to 130° in exterior angle by a hand pressure in the cleaning/polishing operation. To be concrete, the swing angle of the rotary shaft of the cleaning/polishing tip 4 is adjusted with a head angle adjustment unit 1. The head angle adjustment unit 1 works in order that the cleaning/polishing tip 4 and a holder 15 thereof can be revolved relative to the distal end of the body 3 in the prescribed angular range about the rotary shaft 14 of the conversion gear 10 as a center of revolution and by the revolution using the adjustment unit 1, a positional (angular) relation of the conversion gear 10 with each of the gears 7 and 9 changes. In other words, with the revolution by any angle, rotation of the micro-motor driving gear 9 is transmitted unchanged to the cleaning/polishing tip driving gear 7 through the conversion gear 10, while the swing angle after the adjustment by revolution is fixedly held by a prescribed locking unit, not shown, such as a clamp screw or a ratchet mechanism. Or alternatively, parts to adjust a swing angle between the cleaning/polishing tip 4 and the shaft of the motor 5 so as to set to various values are prepared and a desired part can selectively be mounted to achieve a desired swing angle of the cleaning/polishing tip 4.

According to the fifth aspect of the present invention, when the cleaning polisher is divided at a dividing section 2 (FIG. 1) into parts, a total outer volume of the cleaning polisher is equal to or less than that of a 20-cigarette package, thereby enabling an automatic cigarette vending machine or the like, in widespread use, to handle the cleaning polishers.

Furthermore, description will be given of a second example with reference to FIG. 5 to FIGS. 24A to 24B.

Figure 5:
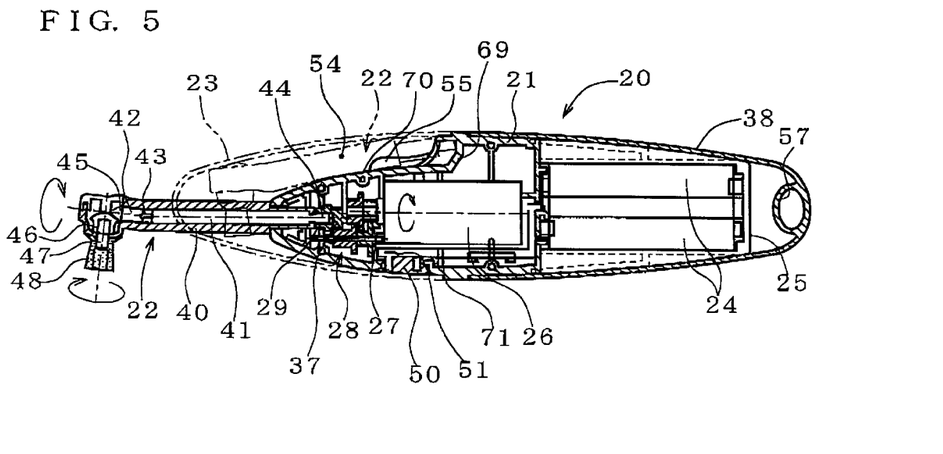
FIG. 5 is a sectional view showing a second example of the present invention.
Figure 6:
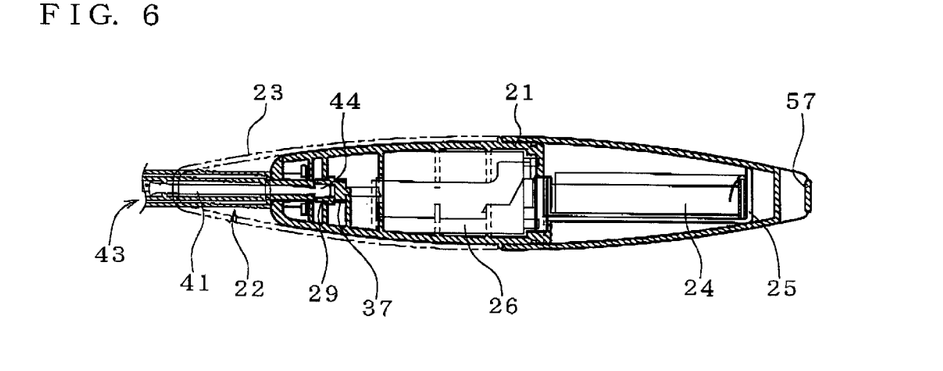
FIG. 6 is a sectional view of the second example with a head member mounting angular position different from FIG. 5 by 90 degrees.

A portable tooth/nail surface cleaning polisher 20 shown in FIGS. 5 and 6 includes: a body 21; a head member 22 with a polishing rotor 48 mounted at the distal end thereof, and a cover 23 enclosing the head member 22 in an accommodated state. An outer shell of the body 21 is formed with a hollow housing made of resin or the like and a battery 24 is inserted in the interior to be mounted in a battery holder 25. The body 21 has somewhat flat shapes such as ellipse in cross-section as shown in cross sections of FIGS. 9A to 9D. Please note that the body 21 can be divided into two parts and a portion of the body covering the battery 24 can be demountable from the other part of the body 21; the covering portion can be regarded as a battery cover 38. A hole 57 is formed at the one end of the body 21 (battery cover 38), the hole 57 is used for hunging the cleaning polisher 20 on a hook or threading a strap.

Figure 7:
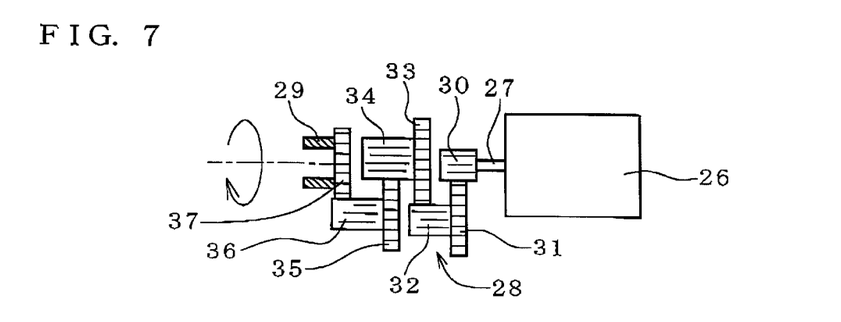
FIG. 7 is a sketch of a side view of a gear train of FIG. 5.
Figure 8:
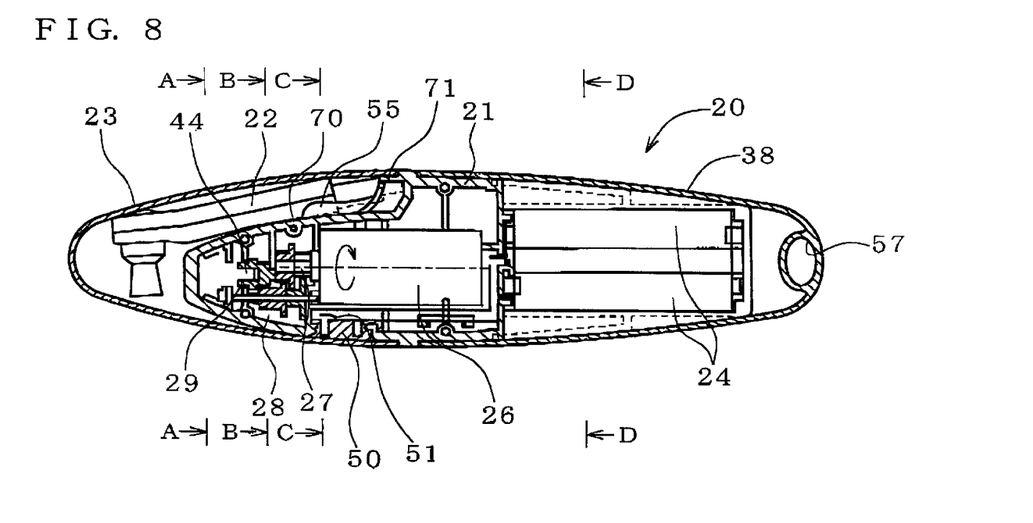
FIG. 8 is a sectional view in a state where a head member is accommodated, corresponding to FIG. 5.
Figure 9A:
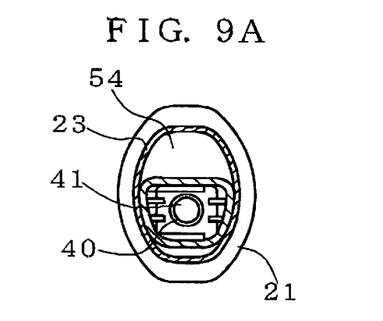
FIG. 9A is a sectional view taken on line A—A of FIG. 8, FIG. 9B on line B—B of FIG. 8, FIG. 9C on line C—C of FIG. 8 and FIG. 9D on line D—D of FIG. 8.
Figure 9B:
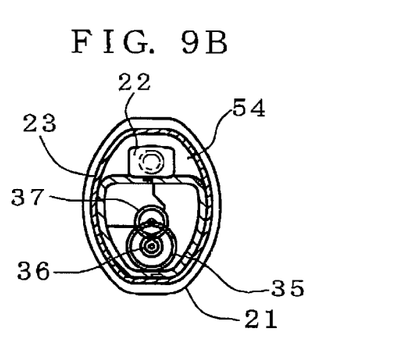
Figure 9C:
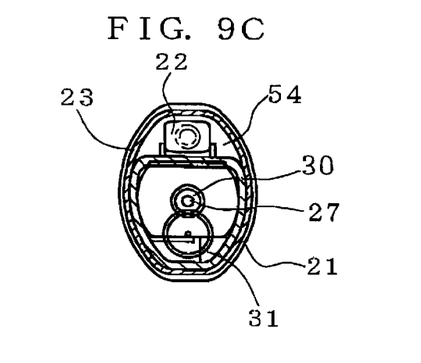
Figure 9D:
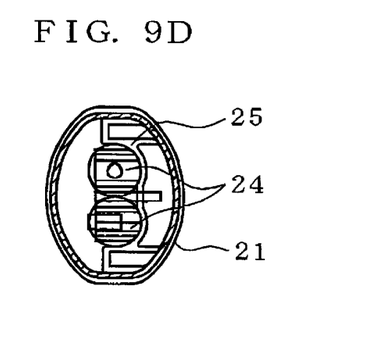

If a side of the body 21 in which the battery 24 is located is called a rear end side by definition, a motor 26 is incorporated in the distal end side (in an almost middle section) forward of the rear end side. Rotation of a rotary shaft 27 of the motor 26 is transmitted to a connection output section 29 through a gear train 28 functioning as reduction gears and moreover, transmitted to a polishing rotor 48 through an internal transmission system of the head member 22. The gear train 28 is constructed from a gear 30 of the motor shaft 27, to gears 31 and 32 in one body, to gears 33 and 34 in one body, to gears 35 and 36 in one body, and to a gear 37, which are sequentially meshed with each other, as shown in FIG. 7, and rotation of the motor shaft 27 is reduced at a prescribed ratio and transmitted to the connection output section 29; then to the polishing rotor 48.

Figure 23A:
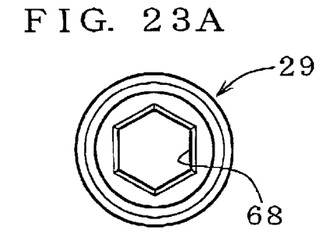
FIG. 23A is a front view of a connection output section of the body side.
Figure 23B:
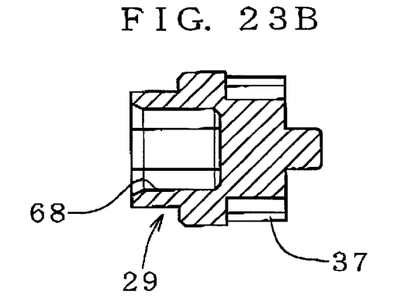
FIG. 23B is a sectional view of FIG. 23A.
Figure 24A:
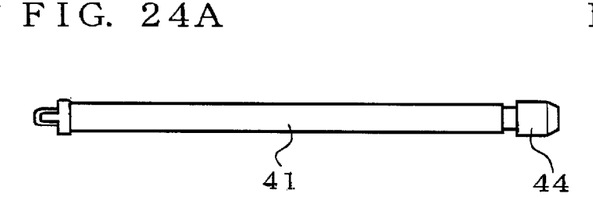
FIG. 24A is a side view of a shaft for transmitting rotation on the head member side and FIG. 24B is a front view of FIG. 2A.
Figure 24B:
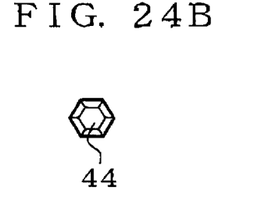

The head member 22 has a long head arm 40, the head arm 40 has a rather flat, hollow section, and a shaft 41 and a shaft 42 for transmitting rotation pass through the interior of the head arm 40 in a state that the shafts 41 and 42 is coupled by a universal joint 43. The shaft 41 has a connection end portion 44 at the rear end side thereof and the connection end portion 44 has a non-circular section such as a hexagon as shown in FIGS. 24A and 24B. The connection end portion 44 is engaged in a non-circular joint hole 68 such as a hexagonal hole of the connection output section 29 shown in FIGS. 23A and 23B and thereby, rotation is transmitted from the connection output section 29 to the shafts 40 and 41 of the head member 22.

Returning to FIG. 5, the shaft 42 is warped upwardly at the distal end thereof to incline relative to the shaft 41 (or example, an angle in the range of 5 to 20 degrees to a straight line of the shaft 41) and corresponding to this warpage, the head arm 40 is bent with an interior obtuse angle so as to form a soft slope. The universal joint 48 couples the shafts 41 and 42 with each other so as to transmit rotation regardless of being non-stationary and being not aligned in line: axial lines of the shafts are intersecting each other.

A bevel gear 45 is attached at the distal end of the shaft 42 and the bevel gear 45 is meshed with a bevel gear 46 fixed to a polishing rotor shaft 47, with the result that rotation is transmitted to the polishing rotor shaft 47 intersecting the shaft 42 at an almost right angle. An end surface of the polishing rotor 48 fixed to the polishing shaft 47 is directed in a direction intersecting the center line of the body 21 (for example, a direction intersecting at an angle in the vicinity of a right angle or a direction inclined by approximately from 3 to 30 degrees of a right angle) and the end surface of the rotor 48 is put into contact with a tooth surface or a nail surface and thereby contaminants attached on the surfaces can be polished off. An outer surface of the polishing rotor 48 can serve as a acting surface for polishing. In this example, a permeable structure that a polishing agent can be guided outside can be adopted: An interior of the polishing rotor 48 is filled with a fluid polishing agent in a proper amount and the polishing rotor 48 is made from a porous material (for example, soft expanded urethane rubber, sponge or the like), or a member with many of slits. By elastic deformation of the polishing rotor 48 when pressing a polishing surface and a centrifugal force produced by the polishing rotor 48, singly or in synergetic combination, the polishing agent contained in the polishing rotor 48 can be gradually supplied to the polishing surface.

In that case, the polishing agent holding member 13 is incorporated in the polishing rotor, the interior of the polishing agent holding member 13 is partitioned with, for example, fills 12 to form the polishing agent storage space 11 and the polishing agent storage space 11 can be filled with the polishing agent before use. The polishing agent holding member 13 is, as described above, made from, for example, a relatively thin, elastically deformable, resin or rubber member, an outer shell of an annular section has a plurality of fins on the inner surface thereof extending inward and spaces between the fins can serve as the polishing agent storage space 11. Alternatively it is possible to form a concave on the end surface of the polishing rotor 48 so that a solid or the like polishing agent can be put into the concave on the surface of the polishing rotor 48, and according to the rotation of the polishing rotor 48 with elastic deformation itself by pressing a polishing surface, the polishing agent can be gradually supplied to the polishing surface.

In a polishing operation, a part of the body 21 shown in FIG. 5 and others, specially the rear end side (including a portion corresponding to the battery over 38) functions as a grip portion and by gripping the portion with a hand, the cleaning polisher is supported. In this case, a switch knob 50 is provided at a position at which a finger, for example, a thumb is placed. By pressing the switch knob 50 with a thumb or other fingers, a switch 51 through which a current passes to the motor 26 is closed and thereby, the motor 26 is driven to rotate the polishing rotor 48. In this case, when the switch knob 50 is kept in a pressed state, the motor continues to be driven. Alternatively, in addition to the switch 51 of this type, a switch circuit can be selected by means of which once a switch is pressed down, the motor 26 continues to be driven even when a finger is released from the knob 50, and when the switch knob 60 is again pressed down, a current flowing to the motor 26 is cut off to cease rotation of the motor 26 and therefore, the polishing rotor 48.

The head member 22 is mounted on the connection output section 29 of the body 21 in a demountable manner, and when a polishing operation is over and the cleaning polisher 20 is stored or carried by a person, the head member 22 is demounted from the connection output section 29 of the body 21 and the head member 22 is temporarily fixed to the body 21 and can further be accommodated in a space formed between the body 21 and the cover 23. In the body 21, the connection output section 29 (together with the motor shaft 27) taking out rotation of the motor 26 is disposed at a position shifted from the longitudinal central line of the body 21 by a prescribed distance such that a space in which the head member 22 is accommodated is formed between the body 21 and the cover 23. A empty space obtained by the shift serves as the accommodating space 54 for accommodating the head member 22 and there is provided a upright wall 69 with a step at the deepest end of the space 54.

Figure 10:
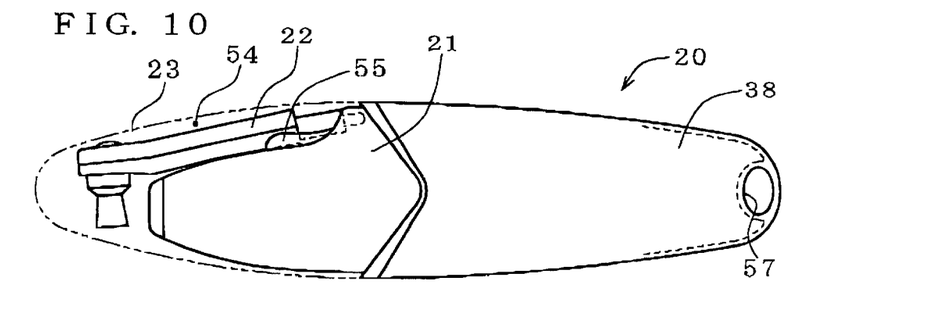
FIG. 10 is a side view in a state where the head member of FIG. 5 is accommodated.
Figure 11:
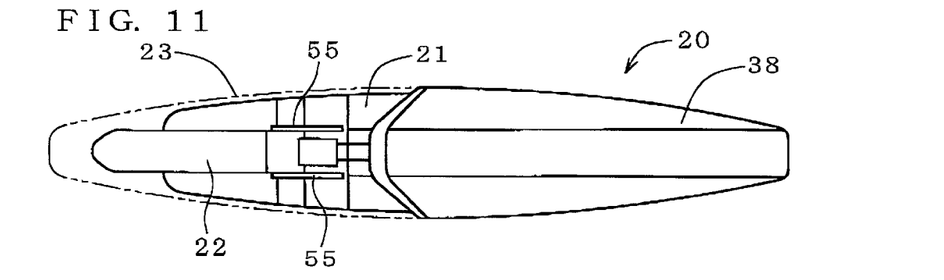
FIG. 11 is a plan view of FIG. 10.
Figure 12:
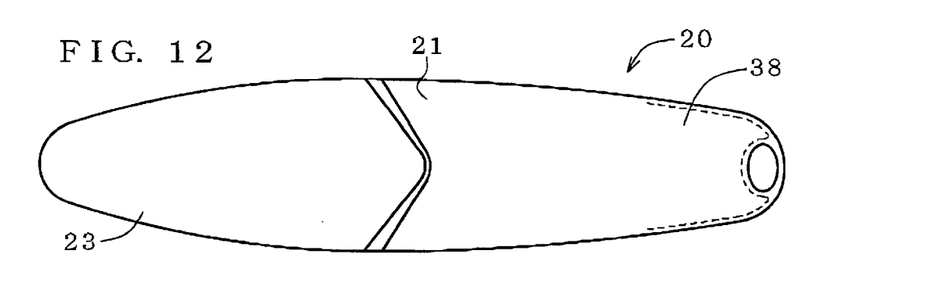
FIG. 12 is a side view in a state where a cover is closed of FIG. 10.
Figure 13:
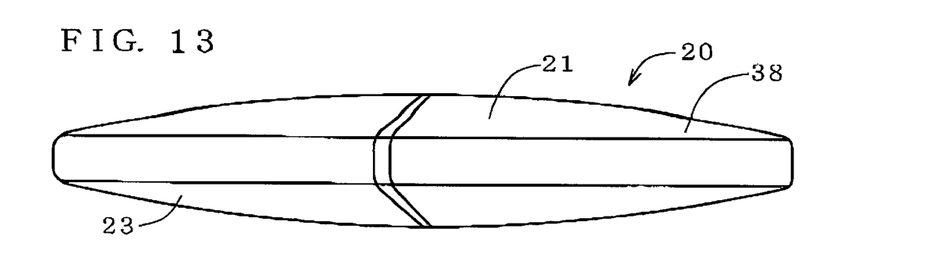
FIG. 13 is a plan view of FIG. 12.

In the accommodating space 54, formed is a head holder 55 holding the head member 22 by pressing in a direction approximately perpendicular to a longitudinal direction thereof from both sides into a stationary state. The head holder 55 of this example is constructed of a pair of protrusions from a surface of the body 21 defining the accommodating space 54 (the surface can be said a rest surface 70 for the head member 22). The head holder 55 provided with the pair of protrusions are, as shown in FIGS. 10 and 11, disposed almost in parallel to each other along a longitudinal direction of the body 21 and a distance between the protrusions is set to be a little smaller than an outer width of the head member 22 (to be more detailed, the head arm 40). The head member 22 is engaged between the protrusions of the head holder 55, for example, in a position facing the deepest end of the accommodating space 54 so as to be in an engagement of clamping to some extent, with the result that the head member 22 is fixed with no play relative to the body 21 in a demountable manner.

In this situation, the cover (accommodating cover) 23 is mounted on the body 21 such that the cover encloses the head member 22. By doing so, the head member 22 is accommodated in a sealed condition between the body 21 and the cover 23. The cover 23 is of the shape of a narrow, long receptacle to sufficiently enclose the entire head member 22, placed sidelong, protruding out from the body 21 and enclose the body 21 by almost one-third to a half of the body 21. An opening end portion of the cover 23 is engaged with a cover mounting section 71 formed close to the middle of the body 21 in a demountable manner such that a proper resistance to demounting of the cover 23 arises.

A shape of the cover 23, especially an internal size and shape thereof, is determined such that in the engaged state, the inner surface of the cover 23 is very close to the head member 22 held in the head holder 55 of the body 21, or alternatively, further presses the head member 22 from outside. With such constructions, since the head member 22 in an accommodated state is hard to be slipped off from the head holder 55 and rattling is also restricted, the accommodated state of the head member 22 can be maintained in a stable manner.

Moreover, the cover 23 encloses the switch knob 50 to control driving and cease of the polishing rotor 48 from outside while mounted on the body 21 in the closed position. With such a construction, even if the switch knob 50 has a chance to enter the pressed-down condition thereof though unintentionally, being carried by a person, a situation where the motor 26 is actually driven is prevented from occurring.

In the situation where the cover 23 is mounted on the body 21, as shown in FIGS. 10 to 13, an outer surface of the body 21 (an outer surface of the battery cover 38) and an outer surface of the cover 23 are continuously connected in an almost planar with each other. Especially, in this example, the outer sources of the body 21 and cover 23 are sectionally connected to each other smoothly along respective curves each of the shape of an arc with a moderate radius and furthermore, the cover 23 and the body 21 (38) are designed to be symmetrical with respect the middle thereof in a longitudinal direction to assume a compact, simple and well-proportioned shape leaving only a dividing line in the middle. With such an outer shape and conditions, the cover 23 forces a user not to be conscious of the presence of the cover integrated into the body 21. Therefore, the cleaning polisher 20 gives the user an impression as if it were one long case and disables a prediction that the head member 22 is accommodated in the interior. In addition to this, the shape of the cleaning polisher has no protrusion and a compact size; therefore, resulting in an advantage to easy to carry putting the cleaning polisher in a bag, a small article receptacle or the like.

Figure 14:
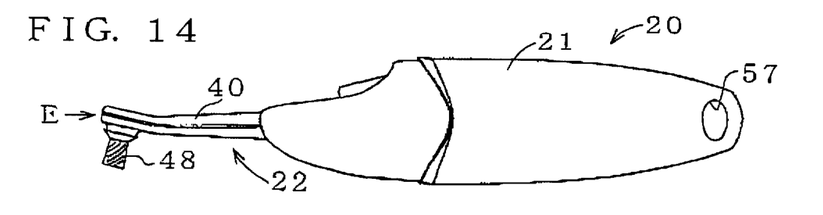
FIG. 14 is a side view in an operative state where a head member is mounted after removing the cover, corresponding to FIG. 5.
Figure 15:
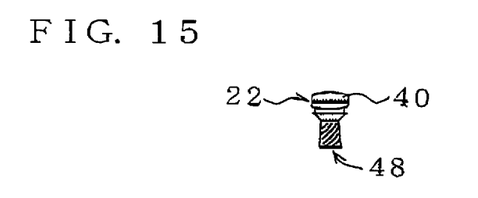
FIG. 15 is a view of a part of the head member of FIG. 14 as seen from the arrow E.
Figure 16:
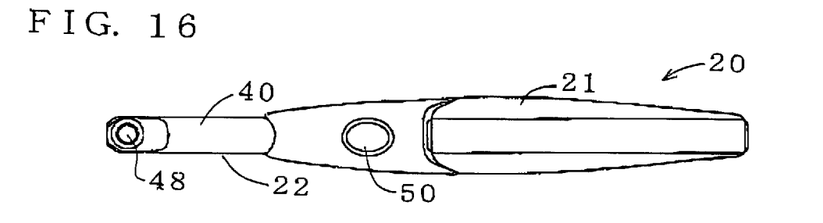
FIG. 16 is a front view of FIG. 14.
Figure 17:
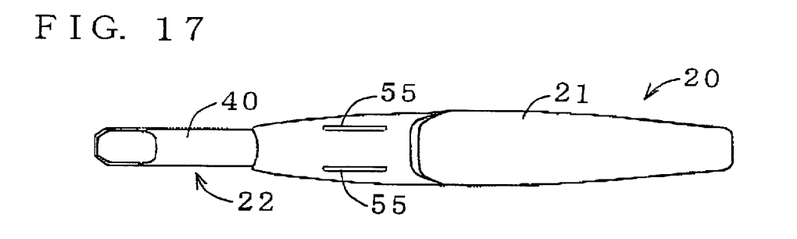
FIG. 17 is a rear plan view of FIG. 14.
Figure 18:
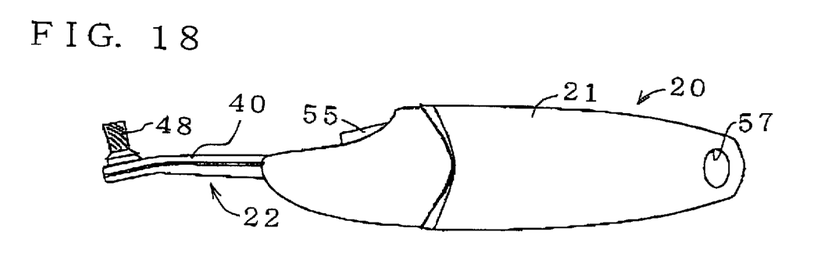
FIG. 18 is a side view of the head member of FIG. 14 with a mounting angular position thereof changed by 180 degrees.
Figure 19A:
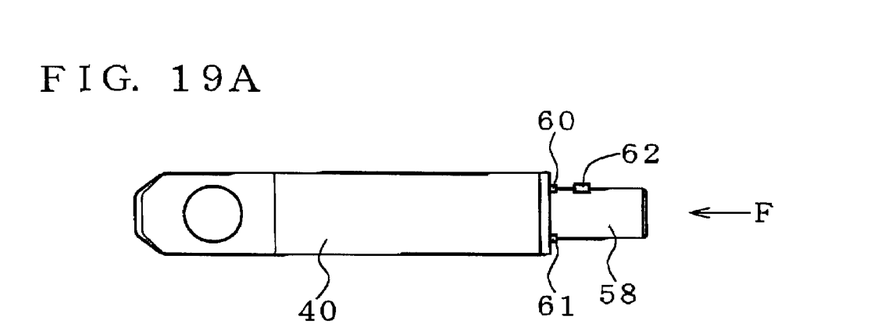
FIG. 19A is a front view of a head arm constituting of an outer shell of a head member and FIG. 19B is a side view showing a part of FIG. 19A.
Figure 19B:
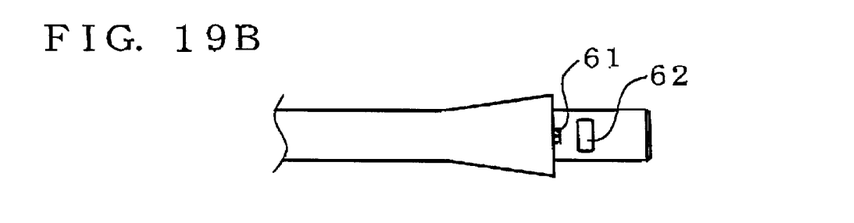
Figure 20:
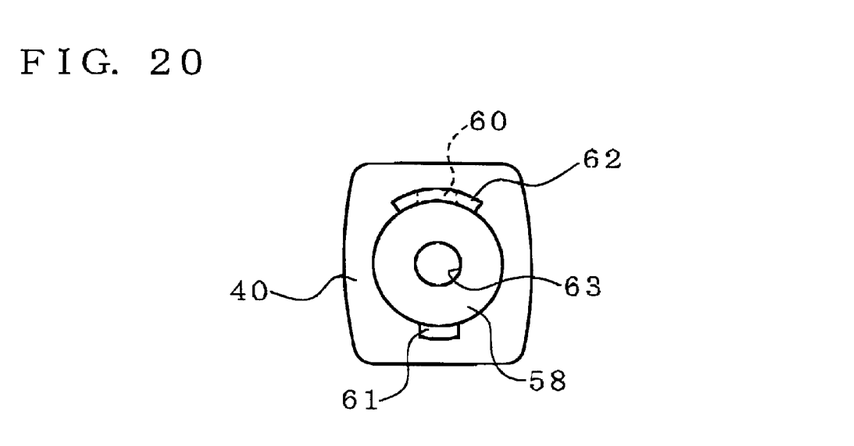
FIG. 20 is an enlarged view showing a part of the head ar of FIG. 19A, as seen from the arrow E.

On the other hand, when the cleaning polisher 20 is in use, the cover 23 is demounted from the body 21 and the head member 22 is further demounted from the head holder 55 of the body 21. By doing so, the head member 22 is connected to the connection output section 29 of the body 21. At this time, while the head member 22 is connected, for example, as shown in FIGS. 14 and 17, the head member 22 can also be mounted on the body 21 such that a direction of the head member 22 can be set in an upside-down position reversing its position of FIG. 14 to a position of FIG. 18. As shown in FIGS. 19 and 20, the head arm 40 being an outer shell of the body of the head member 22 has a section of the shape of a polygon such as a rectangle except for the base end side, but has a cylindrical engaging section (of a circular section) 58 on the base end side of the head arm 40, though a section of the engaging section 58 may also be non-circular.

A stopper 62 protruding a little outward from an outer surface of the engaging section 58 is formed at an intermediate position in an axial direction of the male engaging section 58 with an angular spread along the outer periphery thereof (in the arc range, for example, of 10 to 90 degrees). In addition to this, convex portions 60 and 61 for positioning are provided at the inner end of the male engaging section 58 at angular intervals of 180 degrees, in other words, provided in symmetry with a center in section of the male engaging section 58. On the other hand, a female engaging hole 64 into which the male engaging section 58 of the head arm 40 is inserted is formed in the body 21 and concave portions 65 and 66 for positioning is formed at angular intervals of 180 degrees along the periphery of an opening serving as an inlet side into which the engaging section 58 is inserted, in other words, in symmetry with respect to a center in section of engaging hole 64.

The above described stopper 62 is formed such that the top thereof protrudes from the inner periphery of the engaging hole 64 a little outward (outward in a radial direction) and in addition to this, the stopper 62 is engaged with the periphery of an opening of the other side thereof (the rear side as viewed from the head arm 40 side), passing forcibly though the engaging hole 64 of the body 21 from the inlet side (the front side) to be engaged as described above and act a preventive action of slipping off of the head arm 40. When a pulling-off force more than at a prescribed level acts on the head arm 40, engagement between the stopper 62 and the opening periphery of the engaging hole 64 is canceled and the engaging section 58 can be pulled out from the engaging hole 64.

Figure 21:
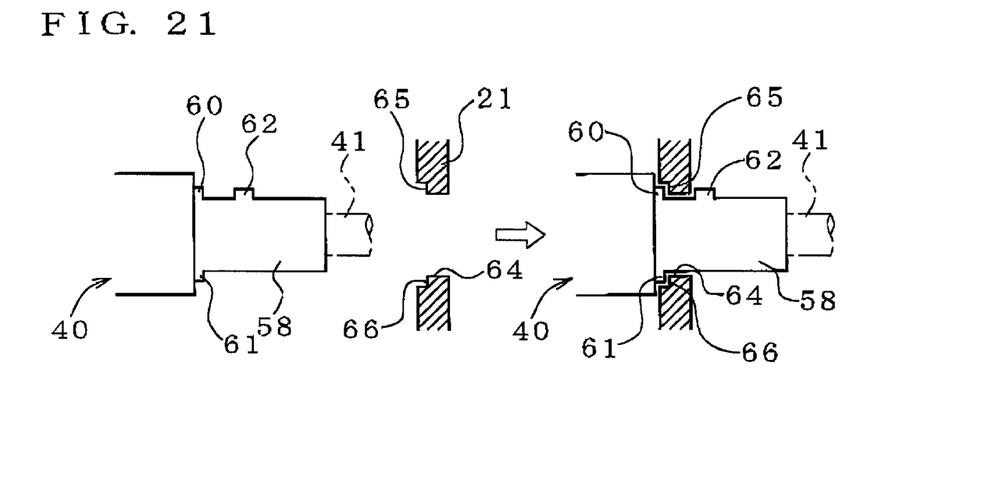
FIG. 21 is side views including sectional views conceptually describing a mounting operation of a head member on the body.

Now, when, as shown in FIG. 21, the engaging section 58 of the head arm 40 (head member 22) is inserted through the engaging hole 64 of the body 21 such that the positioning convex portions 60 and 61 of the former coincide with the positioning concave portions 65 and 66 of the latter in angular position around the engaging section 58, the positioning convex portions 60 and 61 are fixed in position in circumferential direction engaging the respective positioning concave portions 65 and 66 and further the stopper 62 is also engaged with the opening periphery of the rear side of the engaging hole 64 to be fixed in position along the axial direction of the engaging section 58. At this time, the connection end 44 of the shaft 41 (FIG. 24) for transmission of rotation held by the head arm 40 is inserted into a joint hole 68 of the connection output section 29 of FIG. 23 in a state where the connection end portion 44 and the connection output section 29 cannot be rotated mutually.

In this example, a coupler, including the connection output section 29 connecting the shaft 41 for transmitting rotation to the body 21 side and the engaging hole 64 connecting the head arm 40 to the body 21 side, is formed coupling the head member 22 to the body 21 in a demountable manner.

Figure 22:
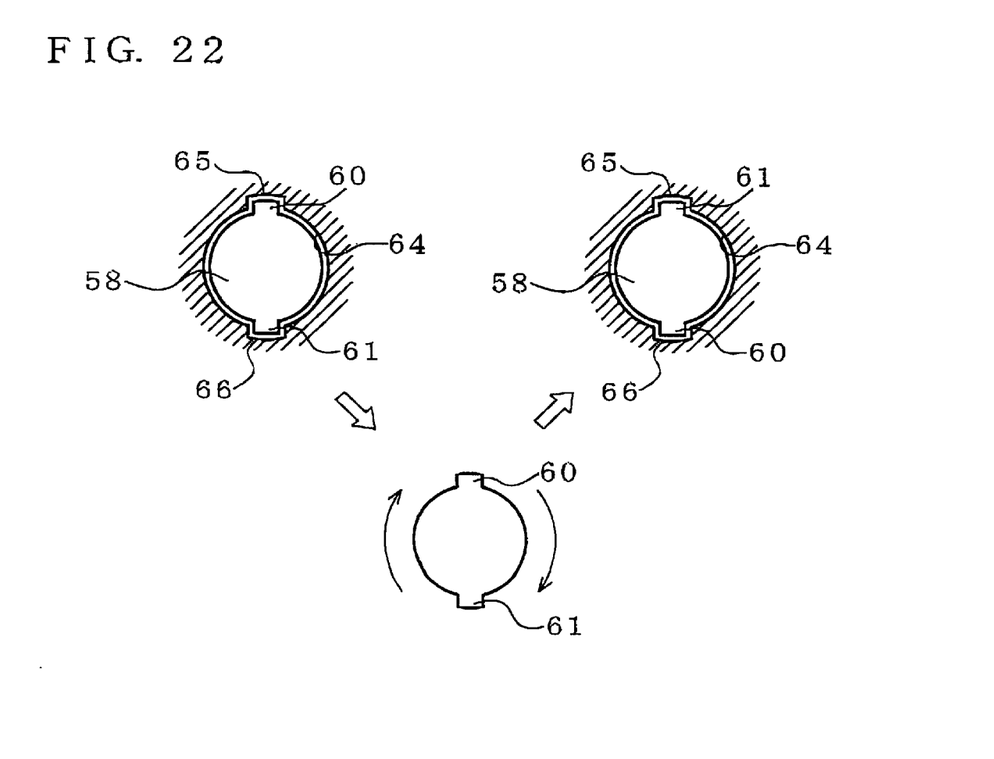
FIG. 22 is sectional views conceptually describing an operation in which a mounting angular position of a head member relative to the body is changed by 180 degrees.

On the other hand, as shown in FIG. 22, when the engaging section 58 of the head arm 40 is pulled out from the engaging hole 64 of the body 21 and a mounting angular position of the head arm 40 (head member 22) is able to be changed by 180 degrees about the axial line of the engaging section 58 to be inserted into the engaging hole 64 again. Then the positioning convex portions 61 and 60 are inserted into the positioning concave portions 65 and 66, respectively, and the head member 22 can be mounted on the body 21 similar to the described above. That is, if a position of the head member 22 shown in FlGS. 14 to 17 is called a first position by definition, a cleaning polisher 20 can be used by reversing the first position by rotation of 180 degrees into a second position shown in FIG. 18.

In the first position, the body 21 is gripped by a hand with a thumb placed on the switch knob, the rotor end surface serving as a main acting surface for polishing of the polishing rotor 48 is directed toward the thumb side and in this position, the front side of teeth can be polished. On the other hand, in the second position shown in FIG. 18, the end surface of the polishing rotor 48 is directed to the other side than the thumb side with the thumb placed on the switch knob 50 and in this position, the rear side of teeth can be polished. As other choices, in polishing a tooth surface and a nail surface, by changing the mounting angular position of the head member 22 to select a direction in which the polishing rotor is directed, a polishing operation can be more effective and easier.

Please note that in FIGS. 19 to 22, one of the positioning convex portions 60 and 61 may be omitted. The two angular positions at 180 degree intervals as in the cases of the positioning portions 65 and 66 can also be varied to other two positions at prescribed angular intervals (for example, at intervals of 90 degrees). Moreover, no limitation is present to two angular positions but a mounting position of the head member 22 can be selected from more than two proper mounting angular positions (for example, 8 angular positions at 45 degree intervals, 36 angular positions at 10 degree intervals, or more than two angular positions at non-equiangular intervals).

A mounting angular position of the head member 22 relative to the body 21 is adjusted by rotation in a stepless manner, which is different from a way that the head member 22 is selectively mounted at any of a plurality of setting angular positions, and a clamp means fixing an angular position after the adjustment may be provided.

Figure 25:
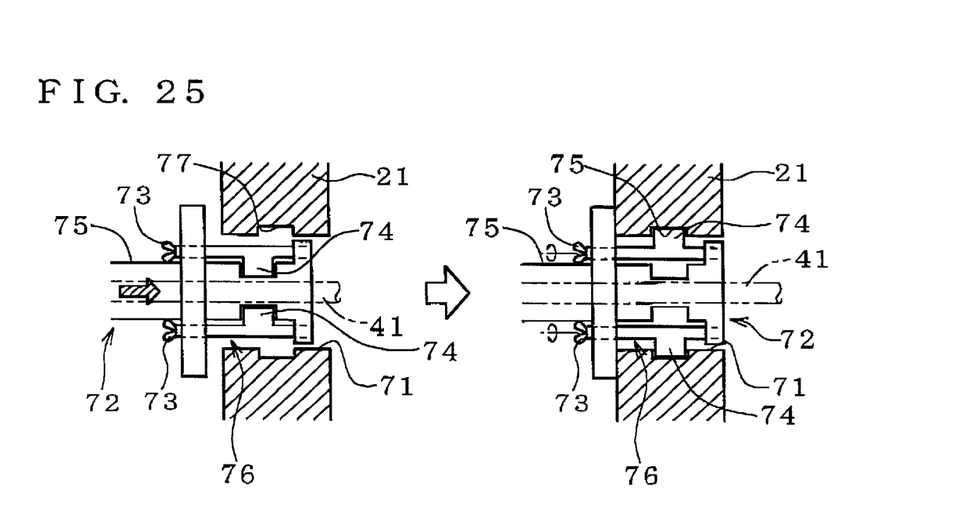
FIG. 25 is side views including sectional views conceptually describing an example in which a head member is fixed to the body at an arbitrary angular position.

FIG. 25 shows the example conceptually and an engaging section 76 engaging in an engaging hole 71 of the body 21 is formed in the base end side of a head arm 76 constituting an outer shell of a head member 72. A proper number of clamp tools 73 equipped with respective cam portions (pressing convex portions) 74 for clamping are placed in the engaging section 76, while on the other hand, clamp grooves 77 in which the cam portions 74 are engaged by a rotation operation of the clamp tool 73 to produce a pressing pressure state are formed on the inner surface of an engaging hole 71 of the body 21. The cam portions 74 of the clamp tool 73 are adjusted to be in an non-operative position and the head member 22 is then inserted into the engaging hole 71, after the insertion, a mounting angular position of the head member 72 is arbitrarily adjusted, thereafter, the cam portions 74 of the clamp tool 73 are moved to respective clamp positions to be forcibly engaged into the clamp grooves 77 in the pressing pressure state. By doing so, the head member 72 is fixed at the above described position after the adjustment of angular positions.

In the examples described following FIG. 1 to FIG. 25, a revolution number of the cleaning polishing tip 4 and the polishing rotor 48 (hereinafter the latter is typically used in description) is preferably in the range of 500 to 2000 rpm, especially approximately in the range of 700 rpm to 1200 rpm. When the revolution number of the polishing rotor 48 faster than the upper limit of 2000 rpm, residues of a polishing operation are easier to fly off to the peripheral area; therefore, the polishing is hard to be practiced with ease and further, the polishing action is apt to be stronger than as expected to make realization of soft polishing to be hard. On the other hand, when the revolution number is slower than the lower limit of 50 rpm, a sufficient polishing action is harder to be exerted. All considered, the above described range can be said to be preferable.

Further, a torque of the polishing rotor 48 is preferably in the range of approximately 8 to 30 mN·m (milli-newton·meter). When the torque is smaller than the 8 mN·m, the polishing rotor 48 cannot be sufficiently pressed on to tooth and nail surfaces (the polishing rotor 48 ceases rotation) while when the torque is larger than 30 mN·m, the motor built in the body is larger in size which hinders realization of a compact type; therefore, the torque of the polishing rotor is preferably determined in the above range. In other words, an output and a revolution number of the motor, a reduction ratio or overdrive ratio of rotation transmitting mechanism are determined so as to sufficiently enable ensuring of a revolution number and a torque of the polishing rotor.

What is claimed is:

1. A portable tooth or nail surface cleaning polisher comprising:

a body portable and gripped by a hand when being used in polishing;

a battery holder incorporated in the body and accommodating a battery;

a motor incorporated in the body and driven by the battery;

a coupler formed in the body and including a rotation output section rotated and driven by the motor;

a head member mounted on the coupler and including a polishing rotor rotating while keeping in contact with a to-be-polished surface;

an accommodating space formed in the body and accommodating the head member demounted from the coupler; and a cover mounted on the body so as to enclose the head member accommodated in the accommodating space from outside; and wherein a head holder for fixing the head member to be accommodated in the accommodating space of the body is formed therein, wherein said head holder for fixing the head member to be accommodated in the accommodating space of the body is held by pressing in a direction approximately perpendicular to a longitudinal direction thereof, and wherein the head holder is constructed of a pair of protrusions from a surface of the body defining the accommodating space.

2. A portable tooth or nail surface cleaning polisher according to claim 1, wherein, the pair of protrusions are disposed almost in parallel to each other along a longitudinal direction of the body and a distance between the protrusions is set to be a little smaller than an outer width of the head member.

* * * * *